US010905759B2

(12) United States Patent
Howley

(10) Patent No.: US 10,905,759 B2
(45) Date of Patent: Feb. 2, 2021

(54) VECTOR-BASED ATTENUATED POXVIRUS VACCINES

(71) Applicant: SEMENTIS LIMITED, Berwick (AU)

(72) Inventor: Paul Howley, Berwick (AU)

(73) Assignee: SEMENTIS LIMITED, Berwick (AU)

(*) Notice: Subject to any disclaimer, the term of this patent is extended or adjusted under 35 U.S.C. 154(b) by 0 days.

(21) Appl. No.: 16/325,539

(22) PCT Filed: Aug. 18, 2017

(86) PCT No.: PCT/AU2017/050879
§ 371 (c)(1),
(2) Date: Feb. 14, 2019

(87) PCT Pub. No.: WO2018/032057
PCT Pub. Date: Feb. 22, 2018

(65) Prior Publication Data
US 2020/0009245 A1 Jan. 9, 2020

(30) Foreign Application Priority Data

Aug. 19, 2016 (AU) .............................. 2016903295

(51) Int. Cl.
| A61K 39/00 | (2006.01) |
| A61K 39/12 | (2006.01) |
| A61P 31/14 | (2006.01) |
| C12N 7/00 | (2006.01) |
| A61K 38/00 | (2006.01) |
| A61K 39/275 | (2006.01) |
| A61P 31/12 | (2006.01) |
| A61K 35/76 | (2015.01) |

(52) U.S. Cl.
CPC ............ *A61K 39/275* (2013.01); *A61K 35/76* (2013.01); *A61P 31/12* (2018.01); *A61K 2039/5256* (2013.01); *A61K 2039/55* (2013.01); *A61K 2039/58* (2013.01)

(58) Field of Classification Search
CPC .............. A61K 39/12; A61K 2039/545; A61K 2039/5254; A61P 31/14; C12N 2770/24134
See application file for complete search history.

(56) References Cited

U.S. PATENT DOCUMENTS 7,767,209 B2 * 8/2010 Staib ..................... A61K 39/12
424/199.1

FOREIGN PATENT DOCUMENTS

| CN | 1418951 | 5/2003 |
| WO | WO 2004/014341 | 2/2004 |
| WO | WO 2012/040474 | 3/2012 |
| WO | WO 2014/138824 | 9/2014 |
| WO | WO2016086980 | * 6/2016 |
| WO | WO2017136419 | 8/2017 |

OTHER PUBLICATIONS

Eldi, Preethi, et al., "Production of a Chikungunya vaccine using a CHO cell and attenuated viral-based platform technology", Molecular Therapy, vol. 25, No. 10, Oct. 2017, pp. 2332-2344.
Extended European Search Report from EP17840633.6 dated Apr. 14, 2020.
Garcia-Arriaza, et al., "A novel poxvirus-based vaccine, MVA-CHIKV, is highly immunogenic and protects mice against chikungunya infection", Journal of Virology, vol. 88, No. 6, Mar. 2014, pp. 3527-3547.
Hayball, J., et al., "A dual Chikungunya and smallpox vaccine derived from a novel, replication-incompetent poxvirus vaccine system provides mice with complete protection from Chikungunya virus and mousepox infection", Eur. J. Immunol., 46(Suppl. 1), Jul. 31, 2016. Abstracts, pp. 809.
Larocca, Rafael, A., et al., "Vaccine protection against Zika virus from Brazil", Nature, 536(7617), Aug. 25, 2016, pp. 474-478.
Prow, Natalie, A., et al., "A vaccinia-based single vector construct multi-pathogen vaccine protects against both Zika and Chikungunya viruses", Nature Communications, 9:1230, 2018, pp. 1-12.
Van Den Doel, Petra, et al., "Recombinant modified vaccinia virus ankara expressing glycoprotein E2 of Chikungunya virus protects AG129 mice against lethal challenge", PLOS Neglected Tropical Diseases, vol. 8, Issue 9, e3101, Sep. 2014, pp. 1-12.
Antoine, G., et al., "The complete genomic sequence of the modified vaccinia Ankara (MVA) strain: comparison with other orthopoxviruses", Virology, 244, 1998, pp. 365-396.
Antoine, G., et al., "Corrigendum to The complete genomic sequence of themodified vaccinia Ankara (MVA) strain: comparison with other orthopoxviruses", Virology, 250, 2006, pp. 501-502.
Garcia-Arriaza, Juan, et al., "A novel poxvirus-based vaccine, MVA-CHIKV, is highly immunogenic and protects mice against Chikungunya Infection", Journal of Virology, vol. 88, No. 6, Mar. 2014, pp. 3527-3547.
Hayball, J., et al., "A dual Chikungunya and smallpox vaccine derived from a novel, replication-incompetent poxvirus vaccine system provides mice with complete protection from Chikungunya virus and mousepox infection", Eur. J. Immunol., 46 (Suppl. 1), 2016, pp. 1-1274.
International Search Report tor PCT/AU2017/050879 dated Oct. 13, 2017.
Prow, Natalie, A., et al., "Poxvirus-based vector systems and the potential for multi-valent and multi-pathogen vaccines", Expert Review of Vaccines, 2018, pp. 1-10.
Van Den Doel, Petra, et al., Recombinant modified vaccinia virus ankara expressing glycoprotein E2 of Chikungunya Virus protects AG129 mice against lethal challenge, PLOS Neglected Tropical Diseases, vol. 8, Issue 9, Sep. 2014, e3101, pp. 1-12.

* cited by examiner

Primary Examiner — Barry A Chestnut
(74) Attorney, Agent, or Firm — Hueschen and Sage

(57) ABSTRACT

The present invention relates to a composition for raising an immune response in animal which decreases the risk of chikungunya and smallpox infection, Zika virus and smallpox infection, and/or chikungunya, Zika virus and smallpox infection. The composition comprises a pharmaceutically acceptable carrier and an attenuated poxvirus, wherein the poxvirus genome comprises a nucleic acid sequence encoding the 26S subgenomic polyprotein of chikungunya virus and/or the PrME of Zika virus.

11 Claims, 6 Drawing Sheets
Specification includes a Sequence Listing.

Figure 1: SCV301A homologous recombination Cassette

Figure 2: F1 and F2 target for homologous recombination in VACV-COP genome

VACV-COP A39R region

Figure 3: the CHIKV-26S insertion site of SCV301A

SCV301A A39R Insertion Site

Figure 4: Deletion of Ecogpt and EGFP by Homologous Recombination

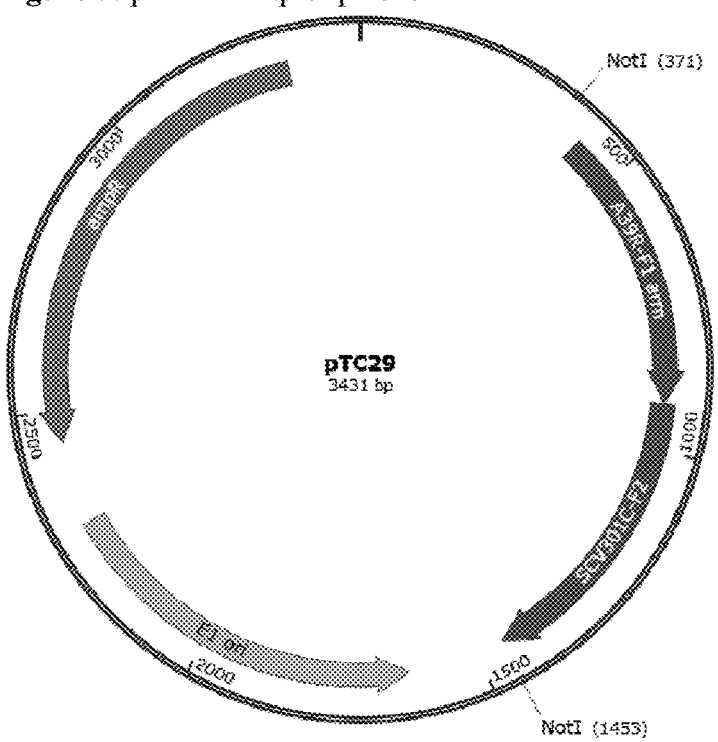
Figure 5: plasmid map of pTC29

Figure 6: D13L Deletion HR Cassette
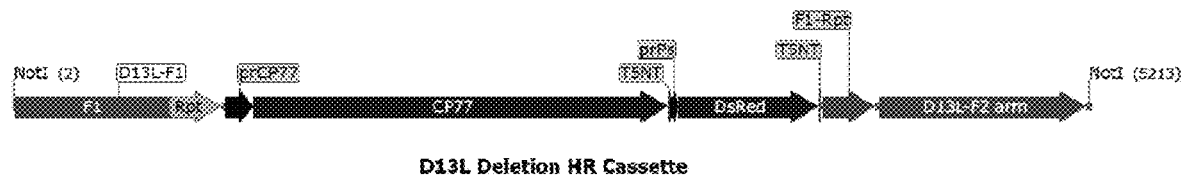
Figure 7: B7R-B8R Deletion HR Cassette
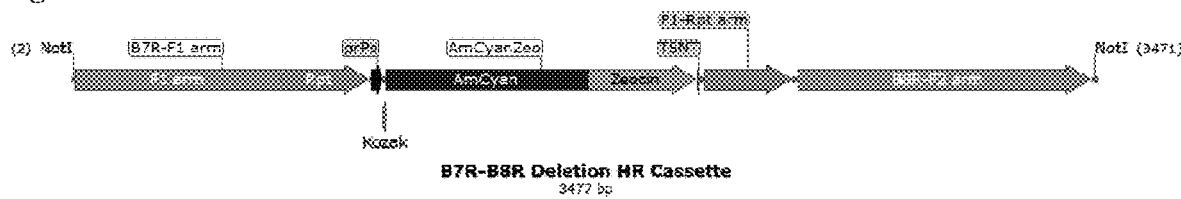

Method of action for homologous recombination with transdominant selection

Figure 9: details of the ZIKV HR cassette

ZIKV-PreME HR cassette
5599 bp

VECTOR-BASED ATTENUATED POXVIRUS VACCINES

FIELD OF THE INVENTION

The present invention relates to an attenuated pox virus vector based vaccine for protection against chikungunya and smallpox, zika virus and smallpox and/or chikungunya, zika virus and smallpox.

BACKGROUND

Bibliographic details of references in the subject specification are listed at the end of the specification.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

All publications mentioned in this specification are herein incorporated by reference in their entirety.

The pox virus family comprises two subfamilies, the Chordopoxvirinae and the Entomopoxvirinae. The Chordopoxvirinae comprises eight genera including the Orthopoxviridae comprising species which infect man (for example, variola virus, the causative agent of smallpox, cowpox virus (which formed the original smallpox vaccine reported by Jenner in 1796), vaccinia virus (used as a second generation smallpox vaccine) and monkeypox virus), and the Avipoxviridae viruses comprising species that infect birds, such as fowlpox and canarypox viruses. In addition to their use as antigens in smallpox vaccines, there is much interest in the use of recombinant vaccinia-based viruses and avipox viruses as a "backbone" vectors. As intra-cytoplasmic vectors, the Orthopoxviridae are able inter alia to deliver foreign antigens to the host cytoplasm and antigen processing pathways that process antigens to peptides for presentation on the cell surface. Such vectors expressing foreign antigens are used in the development of vaccines for diseases such as AIDS, tuberculosis, malaria and cancer which have proven difficult to treat by other vaccination strategies.

The Chordopoxvirinae have linear double-stranded DNA genomes ranging in size from 130 kb in parapoxviruses to over 300 kb in avipoxviruses and their life cycle in the host is spent entirely in the host cell cytoplasm. The poxviruses operate substantially independently of their host cell and host cell molecules, especially for processes involved in early mRNA synthesis. However, host molecules appear to be used for the initiation or termination of intermediate and late viral transcription. The poxviruses produce structurally diverse "host range factors" which specifically target and manipulate host signaling pathways to permit cellular conditions allowing viral replication. Most poxviruses can bind and infect mammalian cells, but whether or not the subsequent infection is permissive (able to produce infectious virions) or non-permissive (substantially unable to produce infectious virions) is dependent upon the specific poxvirus and specific cell type involved. There is currently a relatively poor understanding at the molecular level of pox virus-host interactions, in particular host-range genes, and which factors are necessary to modulate the relationship to facilitate both viral and cellular propagation. For a review of host range genes reference may be made to Werden et al. 2008 incorporated herein in its entirety.

Observations on strains of vaccinia relevant to their use as small pox vaccines and subsequently as viral vectors, have been published from the early 1960's through to the present day. Certain strains of vaccinia, including strains employed as small pox vaccines, are able to propagate in human cells and therefore represent health risks, such as the development of viral encephalitis. With a view to developing a safer vaccine, a vaccinia strain from Ankara (referred to as "CVA") was passaged more than 500 times in non-human cells. During this process the vaccinia genome changed substantially involving the development of at least six major deletions compared to the original CVA genome. The modified virus was less pathogenic in man but still able to engender a protective immune response. This attenuated vaccinia virus is referred to as MVA (Modified Vaccinia Ankara) and is also categorized by passage number, as viruses with different passage numbers were found to be genetically and phenotypically distinct. However, by passage number 515 MVA515 was understood to be genetically stable. In the early 1990s, it was observed that MVA strains, such MVA572, and its derivative, MVA F6 were able to express vaccinia proteins and heterologous (recombinant) proteins at high levels in non-permissive cells (in which the virus will not propagate), enabling the development of MVA as a vector for heterologous molecules of interest, such as those encoding antigens for vaccine or therapy delivery.

More recently, attempts have been made to produce a modified vaccinia virus with the qualities of MVA by introducing the six large known deletions of MVA into CVA. Interestingly, this did not result in a virus with the attenuated qualities of MVA. It was proposed that the absence of host range genes might be responsible for the observed attenuation, however this has not been substantiated (see for example, Meyer et al., Journal of General Virology (1991) 72:1031-1038.

The poxviruses constitute a large family of viruses characterized by a large, linear dsDNA genome, a cytoplasmic site of propagation and a complex virion morphology. Vaccinia virus is the representative virus of this group of virus and the most studied in terms of viral morphogenesis. Vaccinia virus virions appear as "brick shaped" or "ovoid" membrane-bound particles with a complex internal structure featuring a walled, biconcave core flanked by "lateral bodies". The virion assembly pathway involves a fabrication of membrane containing crescents which develop into immature virions (IVs), and then evolve into mature virions (MVs). Over 70 specific gene products are contained within the vaccinia virus virion, where the effects of mutations in over 50 specific genes on vaccinia virus assembly are now described.

Vaccinia virus enter cells by fusion of its surface membranes with the plasma membrane of the host cell, releasing the core (and lateral bodies) into the cytoplasm and activating the virus' transcriptional program. The virion cores contain the full complement of virus-coded enzymes required for synthesis and modification of early mRNA. Early genes encode enzymes required for DNA propagation, and thus as early gene expression peaks, viral DNA propagation ensues in cytoplasmic sites termed "factories." Early genes also encode intermediate transcription factors, and intermediate genes, in turn, encode late transcription factors, so that intermediate and late genes are expressed in succession after the prerequisite initiation of viral DNA propagation. Thus, the full complement of viral genes are transcribed in a temporal cascade, with the early, intermediate and late classes being distinguished by class-specific transcriptional promoters and virally encoded transcription factors. Further-more, only propagated genomes are competent templates for intermediate and late transcription. These two classes of genes together encode virion structural proteins, virion enzymes, and assembly factors and are required for assembly of new progeny virus particles.

Shortly after viral uptake and early expression infection-specific cytoplasmic domains form within the cell that are uniform in density and are sometimes surrounded by endoplasmic reticulum (ER) derived cisternae which increase in size with time. These domains represent sites of viral DNA propagation and are often called "viral factories".

Viral assembly starts with the formation of rigid crescent-shaped structures (cupules in three dimensions) within the viral factories. In high resolution electron micrographs the outer layer of these crescent shaped structures are composed of regularly spaced projections termed "spicules". Crescents apparently grow in length while maintaining the same curvature until they become closed circles (spheres in three dimensions) called immature virions (IV). IV are filled with "viroplasm" material that is uniform in density but discernibly more electron dense than the surrounding factory. As the IVs form uptake of encapsidated DNA also takes place: these are seen in electron micrographs as electron dense, round or ovoid subdomain within the IVs called a "nucleoid". IVs that contain nucleoids of condensed DNA that are often referred to as "IVN." Maturation of several virion protein precursors via proteolytic cleavage is required for the morphogenesis of IVN to mature virions (MV). The majority of mature virions are found outside factories and may exist in clusters either at the periphery of a factory or apparently separated by a significant distance from the nearest factory.

Poxvirus virions exist in three infectious forms: mature virions (MV), wrapped virions (WV), and extracellular virions (EV). MV, the simplest form of the virus, are membrane coated particles containing a biconcave, DNA-containing core flanked by lateral bodies, which fill the concavities of the core. MV are normally found exclusively inside cells and are liberated only by cell lysis. WV consist of MV which are surrounded by two additional lipid bilayers derived from trans-Golgi cisternae. WV, whose outer membranes contain characteristic viral proteins, are precursors of EV and are also found within the cell. EV consist of WV which have been exocytosed via fusion of the outermost WV membrane with the plasma membrane, leaving an MV wrapped in one additional membrane. A fraction of EV are found attached to the cell surface, while some are found free in the extracellular medium. EV are thought to be important for spread of the virus within an organism.

Chikungunya is an infection caused by the chikungunya virus. It features sudden onset fever usually lasting two to seven days, and joint pains typically lasting weeks or months but sometimes years. The mortality rate is a little less than 1 in 1000, with the elderly most likely to die.

The virus is passed to humans by mosquitoes. Animal reservoirs of the virus include monkeys, birds, cattle, and rodents. This is in contrast to dengue, for which only primates are hosts.

The best means of prevention is overall mosquito control and the avoidance of bites by mosquitoes in countries where the disease is common. However, a vaccine which provides protection from this disease would be very desirable.

Zika virus (ZIKV) is a member of the Flavivurus genus of the Flaviviridae family and is a positive single strange RNA virus that is transmitted mainly by the *Aedes aegypti* mosquito, which also carries the dengue and chikungunya viruses. To a lesser extent Zika can also be spread by *Aedes albopictus*, whose distribution reaches far into temperate zones.

Zika virus was first discovered in a monkey in the Zika forest of Uganda in 1947 and this virus has until recently been little more than a scientific curiosity. Around 80% of those infected seem to show no symptoms, and the remainder have no more than a mild illness that resolves within a few days. Originally restricted to small outbreaks in Africa and Asia, the virus spread out in to the Pacific in 2007 to the island of Yap in Micronesia. In 2013, an outbreak in French Polynesia caused 28,000 infections. It is thought that the current outbreak in the Americas arrived from Polynesia. The virus may have been introduced to Brazil during the 2014 FIFA World Cup or a canoe race where Polynesian athletes competed. Since then, the virus has spread through several Latin American countries, including Colombia, Mexico, Paraguay and Venezuela.

Two ZIKV genetic lineages have been described so far, African and Asian. The strains isolated from samples in Brazil between 2015 and 2016 resembled those of Asian strains, particularly the French Polynesia strain [Baronti et al., 2014, Complete coding sequence of Zika virus from a French Polynesia outbreak in 2013. Genome Announc 2: e00500-e00514; Brasil et al., 2016, Zika virus outbreak in Rio de Janeiro, Brazil: Clinical characterization, epidemiological and virological aspects. PLoS Negl Trop Dis 10:e0004636; Faria et al., 2016, Zika virus in the Americas: Early epidemiological and genetic findings. Science 352: 345-349; Giovanetti et al., 2016, Zika virus complete genome from Salvador, Bahia, Brazil. Infect Genet Evol.].

The reference ZIKV strain of the African lineage MR766 differs from the Asian lineage in that the conserve glycosylation site at ASN 153/154 of the envelope protein has been deleted (see FIG. 3 of Sirohi et al 2016, The 3.8 Å resolution cryo-EM structure of Zika virus. Science, 352 (6284): 467-70) giving rise a non-glycosylate E protein in the MR766 strain. This lack of glycosylation does not seem to affect the infectivity of the Zika virus but could play role in virulence and may provide a reason why the Asian strains seem to be more virulent than MR766, however, to date this has not been proven.

For the design of the SCV based vaccines, the antigenic sequences for these vaccines were based on the Asian lineage. The PrME (prMembrane plus envelope) polyprotein sequence was used as the vaccine antigen the vaccine.

SUMMARY

The present inventors have found that by use an attenuated pox virus which has been engineered such that its genome comprises a nucleic acid sequence encoding the 26S subgenomic polyprotein of chikungunya virus and/or the PrME of Zika virus that a composition can be obtained which decreases the risk of chikungunya and smallpox infection, Zika virus and small pox infection, an/or chikungunya, Zika virus and smallpox infection.

Accordingly in a first aspect the present invention provides a composition for raising an immune response in animal which decreases the risk of chikungunya and smallpox infection, the composition comprising a pharmaceutically acceptable carrier and an attenuated poxvirus, wherein the poxvirus genome comprises a nucleic acid sequence encoding the 26S subgenomic polyprotein of chikungunya virus.

In a second aspect the present invention provides a composition for raising an immune response in animal which decreases the risk of zika virus infection and smallpox infection, the composition comprising a pharmaceutically acceptable carrier and an attenuated poxvirus, wherein the poxvirus genome comprises a nucleic acid sequence encoding the PrME polyprotein of zika virus.

In a third aspect the present invention provides a composition for raising an immune response in animal which decreases the risk of chikungunya and zika virus and smallpox infection, the composition comprising a pharmaceutically acceptable carrier and an attenuated poxvirus, wherein the poxvirus genome comprises a nucleic acid sequence encoding the 26S subgenomic polyprotein of chikungunya virus and a nucleic acid sequence encoding the PrME polyprotein of zika virus.

In a fourth aspect the present invention provides a method of inducing a protective immune response in a subject against against chikungunya and smallpox, smallpox and zika virus infection and/or chikungunya, smallpox and zika virus infection the method comprising administering to the subject the composition of the first, second or third aspect of the present invention.

In a fifth aspect the present invention provides the use of the composition of the first, second or third aspect of the present invention in the preparation of a medicament for inducing a protective immune response in a subject against chikungunya and smallpox, smallpox and zika virus infection and/or chikungunya, smallpox and zika virus infection.

BRIEF DESCRIPTION OF FIGURES

FIG. 1. SCV301A homologous recombination cassette.
FIG. 2. F1 and F2 target for homologous recombination in VACV-COP genome.
FIG. 3. CHIKV-26S insertion site of SCV301A.
FIG. 4. Deletion of Ecogpt and EGFP by homologous recombination.
FIG. 5. Plasmid Map of pTC29.
FIG. 6. Deletion HR cassette.
FIG. 7. B7R-B8R deletion HR cassette.
FIG. 9. ZIKR HR cassette.

DETAILED DESCRIPTION

Figure 8:
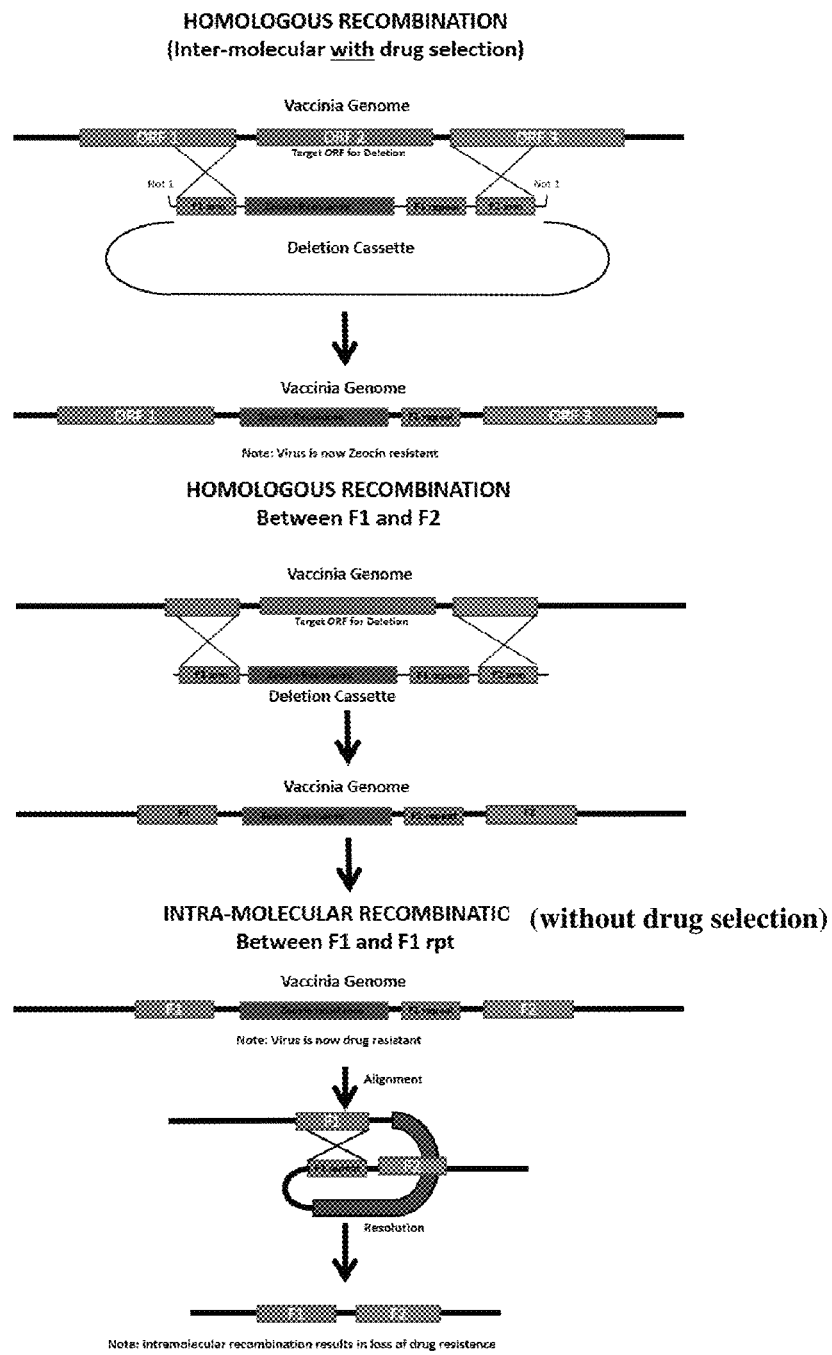
FIG. 8. Method of action of homologous recombination with transdominant selection.

The subject invention is not limited to particular procedures or agents, specific formulations of agents and various medical methodologies, as such may vary. The terminology used herein is for the purpose of describing particular embodiments only and is not intended to be limiting. Unless defined otherwise, all technical and scientific terms used herein have the same meanings as commonly understood by one of ordinary skill in the art to which this invention belongs.

Any materials and methods similar or equivalent to those described herein can be used to practice or test the present invention. Practitioners are particularly directed to: Sambrook et al., (1989) Molecular Cloning: A Laboratory Manual, 2nd ed., Cold Spring Harbor Press, Plainsview, N.Y.; Ausubel et al. (1999) Current Protocols in Molecular Biology (Supplement 47), John Wiley & Sons, New York; Murphy et al. (1995) Virus Taxonomy Springer Verlag: 79-87, Mahy Brian W J and Kangro O Hillar (Eds): Virology Methods Manual 1996, Academic Press; and Davison A J and Elliott R M (Eds): Molecular Virology, A practical Approach 1993, IRL Press at Oxford University Press; Perkus et al., Virology (1990) 179(1):276-86 or definitions and terms of the art and other methods known to the person skilled in the art.

Although any methods and materials similar or equivalent to those described herein can be used in the practice or testing of the present invention, preferred methods and materials are described. For the purposes of the present invention, the following terms are defined below.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. In the context of attenuated orthopox vectors, the subject vectors are modified for attenuation by comprising deletion of an essential maturation or assembly gene however, further modification such as to vector an antigen or other protein is encompassed.

By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein the singular forms "a", "an" and "the" include plural aspects unless the context clearly dictates otherwise. Thus, for example, reference to "a cell" includes a single cell, as well as two or more cells; reference to "an organism" includes one organism, as well as two or more organism; and so forth. In some embodiments, "an" means "one or more than one".

As used herein, "and/or" refers to and encompasses any and all possible combinations of one or more of the associated listed items, as well as the lack of combinations when interpreted in the alternative (or).

"Attenuation" or "attenuated" as used herein means a reduction of viral vector virulence. Virulence is defined as the ability of a virus to cause disease in a particular host. A poxviral vector that is unable to produce infectious viruses may initially infect cells but is unable substantially to replicate itself fully or propagate within the host or cause a condition. This is desirable as the vector delivers its protein or nucleic acid to the host cell cytoplasm, but does not harm the subject.

By "control element" or "control sequence" is meant nucleic acid sequences (e.g., DNA) necessary for expression of an operably linked coding sequence in a particular poxvirus, vector, plasmid or cell. Control sequences that are suitable for eukaryotic cells include transcriptional control sequences such as promoters, polyadenylation signals, transcriptional enhancers, translational control sequences such as translational enhancers and internal ribosome binding sites (IRES), nucleic acid sequences that modulate mRNA stability, as well as targeting sequences that target a product encoded by a transcribed polynucleotide to an intracellular compartment within a cell or to the extracellular environment.

Where sequences are provided, corresponding sequences are encompassed. By "corresponds to" "corresponding" or "corresponding to" is meant a nucleic acid sequence that displays substantial sequence identity to a reference nucleic acid sequence (e.g., at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence identity to all or a portion of the reference nucleic acid sequence) or an amino acid sequence that displays substantial sequence similarity or identity to a reference amino acid sequence (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence similarity or identity to all or a portion of the reference amino acid sequence).

By "effective amount", in the context of treating or preventing a condition or for modulating an immune response to a target antigen or organism is meant the administration of an amount of an agent (e.g., an attenuated orthopox vector as described herein) or composition comprising same to an individual in need of such treatment or prophylaxis, either in a single dose or as part of a series, that is effective for the prevention of incurring a symptom, holding in check such symptoms, and/or treating existing symptoms, of that condition or for modulating the immune response to the target antigen or organism. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

As used herein, the terms "encode," "encoding" and the like refer to the capacity of a nucleic acid to provide for another nucleic acid or a polypeptide. For example, a nucleic acid sequence is said to "encode" a polypeptide if it can be transcribed and/or translated to produce the polypeptide or if it can be processed into a form that can be transcribed and/or translated to produce the polypeptide. Such a nucleic acid sequence may include a coding sequence or both a coding sequence and a non-coding sequence. Thus, the terms "encode," "encoding" and the like include an RNA product resulting from transcription of a DNA molecule, a protein resulting from translation of an RNA molecule, a protein resulting from transcription of a DNA molecule to form an RNA product and the subsequent translation of the RNA product, or a protein resulting from transcription of a DNA molecule to provide an RNA product, processing of the RNA product to provide a processed RNA product (e.g., mRNA) and the subsequent translation of the processed RNA product.

The term "endogenous" refers to a gene or nucleic acid sequence or segment that is normally found in a host organism.

The terms "expressible," "expressed," and variations thereof refer to the ability of a cell to transcribe a nucleotide sequence to RNA and optionally translate the mRNA to synthesize a peptide or polypeptide that provides a biological or biochemical function.

As used herein, the term "gene" includes a nucleic acid molecule capable of being used to produce mRNA optionally with the addition of elements to assist in this process. Genes may or may not be capable of being used to produce a functional protein. Genes can include both coding and non-coding regions (e.g., introns, regulatory elements, promoters, enhancers, termination sequences and 5' and 3' untranslated regions).

The terms "heterologous nucleic acid sequence," "heterologous nucleotide sequence," "heterologous polynucleotide," "foreign polynucleotide," "exogenous polynucleotide" and the like are used interchangeably to refer to any nucleic acid (e.g., a nucleotide sequence comprising an IRES) which is introduced into the genome of an organism by experimental manipulations and may include gene sequences found in that organism so long as the introduced gene contains some modification (e.g., a point mutation, deletion, substitution or addition of at least one nucleotide, the presence of a endonuclease cleavage site, the presence of a loxP site, etc.) relative to the viral genomic sequence before the modification.

The terms "heterologous polypeptide," "foreign polypeptide" and "exogenous polypeptide" are used interchangeably to refer to any peptide or polypeptide which is encoded by an "heterologous nucleic acid sequence," "heterologous nucleotide sequence," "heterologous polynucleotide," "foreign polynucleotide" and "exogenous polynucleotide," as defined above.

The term "protective immune response" means an immune response which prevents, or decreases the risk or severity of, chikungunya and/or small pox infection.

The pox virus vector of the present invention is preferably propagated in a mammalian cell. Details of the mammalian cells which can be used in the present invention are provided in PCT/AU2014/050330, the disclosure of which is incorporated herein by cross reference.

In some embodiments, the mammalian cell is a human cell, a primate cell, a hamster cell or a rabbit cell.

Cells may be unicellular, or can be grown in tissue culture as liquid cultures, monolayers or the like. Host cells may also be derived directly or indirectly from tissues or may exist within an organism including animals.

It will be understood that "inducing" an immune response as contemplated herein includes eliciting or stimulating an immune response and/or enhancing a previously existing immune response.

The term "operably connected" or "operably linked" as used herein refers to a juxtaposition wherein the components so described are in a relationship permitting them to function in their intended manner. For example, a transcriptional control sequence "operably linked" to a coding sequence refers to positioning and/or orientation of the transcriptional control sequence relative to the coding sequence to permit expression of the coding sequence under conditions compatible with the transcriptional control sequence. In another example, an IRES operably connected to an orthopox virus coding sequence refers to positioning and/or orientation of the IRES relative to the orthopox virus coding sequence to permit cap-independent translation of the orthopox virus coding sequence.

As used here the terms "open reading frame" and "ORF" are used interchangeably herein to refer to the amino acid sequence encoded between translation initiation and termination codons of a coding sequence. The terms "initiation codon" (e.g., ATG) and "termination codon" (e.g., TGA, TAA, TAG) refer to a unit of three adjacent nucleotides ('codon') in a coding sequence that specifies initiation and chain termination, respectively, of protein synthesis (mRNA translation).

The terms "polynucleotide," "polynucleotide sequence," "nucleotide sequence," "nucleic acid" or "nucleic acid sequence as used herein designate mRNA, RNA, cRNA, cDNA or DNA. The term typically refers to polymeric form of nucleotides of at least 10 bases in length, either ribonucleotides or deoxynucleotides or a modified form of either type of nucleotide. The term includes single and double stranded forms of RNA or DNA.

"Polypeptide," "peptide," "protein" and "proteinaceous molecule" are used interchangeably herein to refer to molecules comprising or consisting of a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

As used herein the term "recombinant" as applied to "nucleic acid molecules," "polynucleotides" and the like is understood to mean artificial nucleic acid structures (i.e., non-replicating cDNA or RNA; or replicons, self-replicating cDNA or RNA) which can be transcribed and/or translated in host cells or cell-free systems described herein. Recombinant nucleic acid molecules or polynucleotides may be inserted into a vector. Non-viral vectors such as plasmid expression vectors or viral vectors may be used. The kind of vectors and the technique of insertion of the nucleic acid construct according to this invention is known to the artisan. A nucleic acid molecule or polynucleotide according to the invention does not occur in nature in the arrangement described by the present invention. In other words, an heterologous nucleotide sequence is not naturally combined with elements of a parent virus genome (e.g., promoter, ORF, polyadenylation signal, ribozyme).

As used herein, the term "recombinant virus" will be understood to be a reference to a "parent virus" comprising at least one heterologous nucleic acid sequence.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software.

The terms "signal sequence" or "signal peptide refers to a short (about 3 to about 60 amino acids long) peptide that directs co- or post-translational transport of a protein from the cytosol to certain organelles such as the nucleus, mitochondrial matrix, and endoplasmic reticulum, for example. For proteins having an ER targeting signal peptide, the signal peptides are typically cleaved from the precursor form by signal peptidase after the proteins are transported to the ER, and the resulting proteins move along the secretory pathway to their intracellular (e.g., the Golgi apparatus, cell membrane or cell wall) or extracellular locations. "ER targeting signal peptides," as used herein include amino-terminal hydrophobic sequences which are usually enzymatically removed following the insertion of part or all of the protein through the ER membrane into the lumen of the ER. Thus, it is known in the art that a signal precursor form of a sequence can be present as part of a precursor form of a protein, but will generally be absent from the mature form of the protein.

"Similarity" refers to the percentage number of amino acids that are identical or constitute conservative substitutions as defined in Table A below. Similarity may be determined using sequence comparison programs such as GAP (Deveraux et al. 1984, Nucleic Acids Research 12: 387-395). In this way, sequences of a similar or substantially different length to those cited herein might be compared by insertion of gaps into the alignment, such gaps being determined, for example, by the comparison algorithm used by GAP.

TABLE A

Exemplary Conservative Amino Acid Substitutions

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., "Current Protocols in Molecular Biology", John Wiley & Sons Inc, 1994-1998, Chapter 15.

The terms "subject," "patient," "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates (e.g., humans, monkeys and apes, and includes species of monkeys such from the genus *Macaca* (e.g., cynomologus monkeys such as *Macaca fascicularis*, and/or rhesus monkeys (*Macaca mulatta*)) and baboon (*Papio ursinus*), as well as marmosets (species from the genus *Callithrix*), squirrel monkeys (species from the genus *Saimiri*) and tamarins (species from the genus *Saguinus*), as well as species of apes such as chimpanzees (*Pan troglodytes*)), rodents (e.g., mice, rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc.), marine mammals (e.g., dolphins, whales), reptiles (snakes, frogs, lizards etc.), and fish. A preferred subject is a human in need of treatment or prophylaxis of a condition. However, it will be understood that the aforementioned terms do not imply that symptoms are present.

The term "transgene" is used herein to describe genetic material that has been or is about to be artificially introduced into a genome of a host organism and that is transmitted to the progeny of that host. In some embodiments, it confers a desired property to a mammalian cell or an orthopox vector into which it is introduced, or otherwise leads to a desired therapeutic or diagnostic outcome.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "wild-type," "natural," "native" and the like with respect to an organism, polypeptide, or nucleic acid sequence, that the organism polypeptide, or nucleic acid sequence is naturally occurring or available in at least one naturally occurring organism which is not changed, mutated, or otherwise manipulated by man.

Variants include nucleic acid molecules sufficiently similar to a referenced molecule or their complementary forms over all or part thereof such that selective hybridisation may be achieved under conditions of medium or high stringency, or which have about 60% to 90% or 90 to 98% sequence identity to the nucleotide sequences defining a referenced poxvirus host range factor over a comparison window comprising at least about 15 nucleotides. Preferably the hybridisation region is about 12 to about 18 nucleobases or greater in length. Preferably, the percent identity between a particular nucleotide sequence and the reference sequence is at least about 80%, or 85%, or more preferably about 90% similar or greater, such as about 95%, 96%, 97%, 98%, 99% or greater. Percent identities between 80% and 100% are encompassed. The length of the nucleotide sequence is dependent upon its proposed function. Homologs are encompassed. The term "homolog" "homologous genes" or "homologs" refers broadly to functionally and structurally related molecules including those from other species. Homologs and orthologs are examples of variants.

Nucleic acid sequence identity can be determined in the following manner. The subject nucleic acid sequence is used to search a nucleic acid sequence database, such as the GenBank database (accessible at web site www.ncbi.nln-.nih.gov/), using the program BLASTM version 2.1 (based on Altschul et al, (1997) *Nucleic Acids Research* 25:3389-3402). The program is used in the ungapped mode. Default filtering is used to remove sequence homologies due to regions of low complexity. The default parameters of BLASTM are used.

Amino acid sequence identity can be determined in the following manner. The subject polypeptide sequence is used to search a polypeptide sequence database, such as the GenBank database (accessible at web site www.ncbi.nln.gov), using the BLASTP program. The program is used in the ungapped mode. Default filtering is used to remove sequence homologies due to regions of low complexity. The default parameters of BLASTP are utilized. Filtering for sequences of low complexity may use the SEG program.

Preferred sequences will hybridise under stringent conditions to a reference sequence or its complement. The term "hybridize under stringent conditions", and grammatical equivalents thereof, refers to the ability of a nucleic acid molecule to hybridize to a target nucleic acid molecule (such as a target nucleic acid molecule immobilized on a DNA or RNA blot, such as a Southern blot or Northern blot) under defined conditions of temperature and salt concentration. With respect to nucleic acid molecules greater than about 100 bases in length, typical stringent hybridization conditions are no more than 25° C. to 30° C. (for example, 10° C.) below the melting temperature (Tm) of the native duplex (see generally, Sambrook et al., (supra); Ausubel et al., (1999)). Tm for nucleic acid molecules greater than about 100 bases can be calculated by the formula $Tm=81.5+0.41\%(G+C-\log(Na^+))$. With respect to nucleic acid molecules having a length less than 100 bases, exemplary stringent hybridization conditions are 5° C. to 10° C. below Tm.

The term "deletion" in the present context removal of all or part of the coding region of the target gene. The term also encompasses any form of mutation or transformation which ablates gene expression of the target gene or ablates or substantially down regulates the level or activity of the encoded protein.

Reference to "gene" includes DNA corresponding to the exons or the open reading frame of a gene. Reference herein to a "gene" is also taken to include: a classical genomic gene consisting of transcriptional and/or translational regulatory sequences and/or a coding region and/or non-translated sequences (i.e. introns, 5'- and 3'-untranslated sequences); or mRNA or cDNA corresponding to the coding regions (i.e. exons) and 5'- and 3'-untranslated sequences of the gene.

By "regulatory element" or "regulatory sequence" is meant nucleic acid sequences (e.g., DNA) necessary for expression of an operably linked coding sequence in a particular host cell. The regulatory sequences that are suitable for prokaryotic cells for example, include a promoter, and optionally a cis-acting sequence such as an operator sequence and a ribosome binding site. Control sequences that are suitable for eukaryotic cells include promoters, polyadenylation signals, transcriptional enhancers, translational enhancers, leader or trailing sequences that modulate mRNA stability, as well as targeting sequences that target a product encoded by a transcribed polynucleotide to an intracellular compartment within a cell or to the extracellular environment.

Chimeric constructs suitable for effecting the present modified mammalian cells comprise a nucleic acid sequence encoding an orthopox host range factor, which is operably linked to a regulatory sequence. The regulatory sequence suitably comprises transcriptional and/or translational control sequences, which will be compatible for expression in the cell. Typically, the transcriptional and translational regulatory control sequences include, but are not limited to, a promoter sequence, a 5' non-coding region, a cis-regulatory region such as a functional binding site for transcriptional regulatory protein or translational regulatory protein, an upstream open reading frame, ribosomal-binding sequences, transcriptional start site, translational start site, and/or nucleotide sequence which encodes a leader sequence, termination codon, translational stop site and a 3' non-translated region. Constitutive or inducible promoters as known in the art are contemplated. The promoters may be either naturally occurring promoters, or hybrid promoters that combine elements of more than one promoter.

Promoter sequences contemplated may be native to mammalian cells or may be derived from an alternative source, where the region is functional in the chosen organism. The choice of promoter will differ depending on the intended host cell. For example, promoters which could be used for expression in mammalian cells include the metallothionein promoter, which can be induced in response to heavy metals such as cadmium, the β-actin promoter as well as viral promoters such as the SV40 large T antigen promoter, human cytomegalovirus (CMV) immediate early (IE) promoter, Rous sarcoma virus LTR promoter, the mouse mammary tumour virus LTR promoter, the adenovirus major late promoter (Ad MLP), the herpes simplex virus promoter, and a HPV promoter, particularly the HPV upstream regulatory region (URR), among others. All these promoters are well described and readily available in the art.

Enhancer elements may also be used herein to increase expression levels of the mammalian constructs. Examples include the SV40 early gene enhancer, as described for example in Dijkema et al. (1985) *EMBO J.* 4:761, the enhancer/promoter derived from the long terminal repeat (LTR) of the Rous Sarcoma Virus, as described for example in Gorman et al., (1982) *Proc. Natl. Acad. Sci. USA* 79:6777 and elements derived from human CMV, as described for example in Boshart et al. (1985) *Cell* 41:521, such as elements included in the CMV intron A sequence.

The chimeric construct may also comprise a 3' non-translated sequence. A 3' non-translated sequence refers to that portion of a gene comprising a DNA segment that contains a polyadenylation signal and any other regulatory signals capable of effecting mRNA processing or gene expression. The polyadenylation signal is characterized by effecting the addition of polyadenylic acid tracts to the 3' end of the mRNA precursor. Polyadenylation signals are commonly recognized by the presence of homology to the canonical form 5' AATAAA-3' although variations are not uncommon. The 3' non-translated regulatory DNA sequence preferably includes from about 50 to 1,000 nts and may contain transcriptional and translational termination sequences in addition to a polyadenylation signal and any other regulatory signals capable of effecting mRNA processing or gene expression.

In some embodiments, the chimeric construct further contains a selectable marker gene to permit selection of cells containing the construct. Selection genes are well known in the art and will be compatible for expression in the cell of interest.

In one embodiment, expression of the orthopox structural or assembly gene is under the control of a promoter. In one non-limiting embodiment the promoter is a cellular constitutive promoter, such as human EF1 alpha (human elongation factor 1 alpha gene promoter), DHFR (dihydrofolate reductase gene promoter) or PGK (phosphoglycerate kinase gene promoter) that direct expression of a sufficient level of CP77 to sustain viral propagation in the absence of significant toxic effects on the host cell. Promoters may also be inducible, such as the cellular inducible promoter, MTH (from a metallothionein gene) viral promoters are also employed in mammalian cells, such as CMV, RSV, SV-40, and MoU3.

The present invention provides a composition comprising an attenuated poxvirus that can be used as a vaccine for inducing protection against Chikungunya and Smallpox virus infection. The terms "attenuation", "attenuated" and the like, as used herein, mean a reduction of viral vector virulence. Virulence is typically defined as the ability of a virus to cause disease in a particular host. For instance, a poxvirus that is unable to produce infectious viruses may initially infect cells but is substantially unable to replicate itself fully or propagate within the host or host cell or cause a disease or condition. This is desirable, as the poxvirus vector can deliver nucleic acid to the host or host cell, but typically does not harm the host or host cell.

The poxvirus family comprises two subfamilies, the Chordopoxvirinae and the Entomopoxvirinae. The Chordopoxvirinae comprises eight genera including the Orthopoxviridae comprising species which infect man while the Entomopoxvirinae infect insects. The Orthopoxviridae includes for example, variola virus which is the causative agent of smallpox, cowpox virus which formed the original smallpox vaccine reported by Jenner in 1796, and vaccinia virus which has been used as a second generation smallpox vaccine. The Avipoxviridae virus comprises species that infect birds, such as fowlpox and canarypox viruses. In addition to their use as antigens in smallpox vaccines, there is much interest in the use of recombinant vaccinia-based viruses and avipox viruses as vectors for delivering and/or expressing heterologous genes of interest. As intra-cytoplasmic vectors, the Orthopoxviridae are able to deliver foreign antigens to the host cytoplasm and antigen processing pathways that process antigens to peptides for presentation on the cell surface. Such vectors expressing foreign antigens are suitable for use in gene therapy and the development of vaccines for a wide range of conditions and diseases.

The poxviruses constitute a large family of viruses characterized by a large, linear dsDNA genome, a cytoplasmic site of propagation and a complex virion morphology. Vaccinia virus is the representative virus of this group of viruses and one of the most studied in terms of viral morphogenesis. Vaccinia virus virions appear as "brick shaped" or "ovoid" membrane-bound particles with a complex internal structure featuring a walled, biconcave core flanked by "lateral bodies". The virion assembly pathway involves a fabrication of membrane containing crescents which develop into immature virions (IVs), and then evolve into mature virions (MVs). Over 70 specific gene products are contained within the vaccinia virus virion, where the effects of mutations in over 50 specific genes on vaccinia virus assembly are now described.

Suitable attenuated poxviruses would be known to persons skilled in the art. Illustrative examples include attenuated Modified Vaccinia Ankara (MVA), NYVAC, avipox, canarypox and fowlpox. Thus, in an embodiment disclosed herein, the attenuated poxvirus is selected from the group consisting of Modified Vaccinia Ankara (MVA), NYVAC, avipox, canarypox and fowlpox. In an embodiment, the attenuated poxvirus is an attenuated vaccinia virus. Illustrative examples of vaccinia strains Copenhagen (COP), Western Reserve (WR), Wyeth, ACAM2000, LC16m8 and Connaught Laboratories (CL).

It would be understood by persons skilled in the art that other orthopoxvirus strains may be modified to produce an attenuated poxvirus. In an illustrative example, an attenuated poxvirus can be produced by modifying (e.g., deleting, substituting or otherwise disrupting the function of) a gene from the poxvirus genome that encodes an endogenous essential assembly or maturation protein. Thus, in an embodiment disclosed herein, the attenuated poxvirus is a modified orthopoxvirus, wherein the modification comprises deletion of a gene encoding an endogenous essential assembly or maturation protein.

In an embodiment, the attenuated poxvirus is a modified vaccinia virus wherein the modification comprises deletion of a gene of the vaccinia virus genome encoding (or otherwise disruption of the function of) an endogenous assembly or maturation protein and wherein the modification transforms a vaccinia vector which propagates (or which may propagate) in a host cell (e.g., a human cell) into an attenuated vaccinia vector which is substantially non-replicative in the host cell. In an embodiment, the essential endogenous assembly or maturation gene is selected from the group consisting of COP-A2.5L, COP-A3L, COP-A4L, COP-A7L, COP-A8R, COP-A9L, COP-A10L, COP-A11R, COP-A12L, COP-A13L, COP-A14L, COP-A14.5L, COP-A15L, COP-A16L, COP-A17L, COP-A21L, COP-A22R, COP-A26L, COP-A27L, COP-A28L, COP-A30L, COP-A32L, COP-D2L, COP-D3R, COP-D6R, COP-D8L, COP-D13L, COP-E8R, COP-E10R, COP-E11L, COP-F10L, COP-F17R, COP-G1L, COP-G3L, COP-G4L, COP-G5R, COP-G7L, COP-G7L, COP-H1L, COP-H2R, COP-H3L, COP-H4L, COP-H5R, COP-H6R, COP-I1L, COP-I2L, COP-I6L, COP-17L, COP-I8R, COP-J1R, COP-J4R, COP-J6R, COP-L1R, COP-L3L, COP-L4R and COP-L5R.

In a preferred embodiment the modification comprises deletion of the D13L gene and/or the K1L gene and/or the A39R gene and/or the B7R-B8R genes.

In a further preferred embodiment the modification comprises deletion of the D13L gene, the A39R gene and the B7R-B8R genes.

In a first aspect the present invention provides a composition for raising an immune response in animal which decreases the risk of chikungunya and smallpox infection, the composition comprising a pharmaceutically acceptable carrier and an attenuated poxvirus, wherein the poxvirus genome comprises a nucleic acid sequence encoding the 26S subgenomic polyprotein of chikungunya virus.

In a second aspect the present invention provides a composition for raising an immune response in animal which decreases the risk of zika virus infection and smallpox infection, the composition comprising a pharmaceutically acceptable carrier and an attenuated poxvirus, wherein the poxvirus genome comprises a nucleic acid sequence encoding the PrME polyprotein of zika virus.

In a third aspect the present invention provides a composition for raising an immune response in animal which decreases the risk of chikungunya and zika virus and smallpox infection, the composition comprising a pharmaceutically acceptable carrier and an attenuated poxvirus, wherein the poxvirus genome comprises a nucleic acid sequence encoding the 26S subgenomic polyprotein of chikungunya virus and a nucleic acid sequence encoding the PrME polyprotein of zika virus.

In a fourth aspect the present invention provides a method of inducing a protective immune response in a subject against against chikungunya and smallpox, smallpox and zika virus infection and/or chikungunya, smallpox and zika virus infection the method comprising administering to the subject the composition of the first, second or third aspect of the present invention.

In a fifth aspect the present invention provides the use of the composition of the first, second or third aspect of the present invention in the preparation of a medicament for inducing a protective immune response in a subject against chikungunya and smallpox, smallpox and zika virus infection and/or chikungunya, smallpox and zika virus infection.

In preferred forms of the current invention the attenuated poxvirus is selected from the group consisting of vaccinia, cowpox, Modified Vaccinia Ankara (MVA), NYVAC, avipox, canarypox and fowlpox. It is preferred that the attenuated poxvirus is a modified orthopoxvirus, wherein the modification comprises deletion of a gene encoding an endogenous essential assembly or maturation protein. It is further preferred that the modification comprises deletion of the D13L gene and preferably further comprises the deletion of the K1L gene.

In certain embodiments the pharmaceutically acceptable carrier comprises an adjuvant. It is preferred that the adjuvant is selected form the group consisting of aluminium hydroxide, aluminium phosphate, potassium aluminium sulfate, calcium phosphate hydroxide, Freund's complete adjuvant, Montanide®, Freund's incomplete adjuvant, iscoms, iscom matrix, ISCOMATRIX™ adjuvant, Matrix M™ adjuvant, Matrix C™ adjuvant, Matrix Q™ adjuvant, AbISCO®-100 adjuvant, AbISCO®-300 adjuvant, ISCO-PREP™, an ISCOPREP™ derivative, adjuvant containing ISCOPREP™ or an ISCOPREP™ derivative, QS-21, a QS-21 derivative, and an adjuvant containing QS-21 or a QS21 derivative.

The various embodiments enabled herein are further described by the following non-limiting examples.

Example 1

Summary of Construction Strategies

Three SCV viruses where constructed prior to constructing SCV1002, the single vectored CHIK/ZIKA vaccine. SCV301C was constructed by replacing the A39R ORF of vaccinia virus Copenhagen strain with a CHIKV-26S expression cassette together with EGFP and Ecogpt expression cassettes. SCV302 was created by deleting the EGFP and Ecogpt cassettes from SCV301C. SCV305, the SCV-CHIK vaccine, was then created by deleting the B7R-B8R ORFs and D13L ORFs from SCV302. Finally, SCV1002, SCV-CHIK/ZIKA vaccine, was created by replacing the B7R-B8R ORFs of SCV302 with a ZIKV-prME expression cassette and deleting the D13L ORF.

Construction of SCV301C (VACV-CHIK)

Description

The Chikungunya vaccine antigen expression cassette in SCV301C (CHIKV-26S) consist of the following element in a linear array:
  vaccinia early/late promoter,
  CHIKV protein coding sequence for the 26S subgenomic polyprotein of the virulent Reunion strain 06_21, pox virus
  and a poxvirus early transcriptional stop sequence.

The CHIKV 26S subgenomic polyprotein when expressed will be processed into the individual structural genes necessary for the formation of virus particles. Since the whole CHIKV genome is not present and the subgenomic RNA will not contain the 5' UTR and 3' UTR, no transcribed viral RNA will be packaged into the newly formed viral particles—in essence, expression of just the 26S subgenomic polyprotein will give rise to virus-like-particle (VLP) devoid of viral genomic RNA. The in vivo expression of the subgenomic polyprotein leading to VLP formation upon vaccination will be favourable for neutralising antibody stimulation—a key correlate of immunity for prophylactic vaccination again CHIKV.

The amino acid sequence for the 26S subgenomic polyprotein in the CHIKV-26S expression cassette was taken from the virulent Reunion strain that genetically changed to broaden its host range for a new mosquito vector (Genbank, Accession Number: AM258992). During an epidemic of Reunion between 2005 and 2006, the virus mutated to broaden its vector-host range to the Asian tiger mosquito (*Aedes albopictus*). The Asian tiger mosquito is the fastest spreading mosquito in the world. Extremely well adapted to living around people and known to travel in used tires. It is found in rural and green urban areas, almost worldwide and is an aggressive daytime biter of humans, domestic and wild animals, and birds. This mosquito has the potential to spread Chikungunya worldwide. The final nucleotide sequence design of the CHIKV-26S protein coding sequence was screened for pox virus early transcriptional motif "TTTTTNT"—none were found. The Pox virus early transcriptional stop sequence TTTTTAT was added immediately after the stop codon. The sequence for CHIKV-26S expression cassette described above is given in SEQ ID NO:1.

To create SCV301C, an homologous recombination cassette was synthesized by GeneArt GmbH that consisted of the CHIKV-26S expression cassette, an enhanced fluorescent green protein expression cassette, an Ecogpt expression cassette all flanked by left and right homologous recombination arms that target the up-stream and down-stream sequences of VACV-COP A39R ORF for homologous recombination as shown in FIGS. 1 and 2 below. Table 1 lists the features of the SCV301A homologous recombination cassette and the sequence details are provided in SEQ ID NO:2.

polyprotein (Genbank accession number: AM258992), under the control of VACV promoters (Chakrabarti et al, 1997), together with a poxvirus expression cassette for the expression of the *E. coli* guanine phosphoribosyltransferease (Ecogpt). Homologous recombination and positive selection of recombinant viruses containing the co-insertion of the Ecogpt expression cassette was undertaken as described in Protocol 6 of Smith (1993) and published in Falkner et al (1988) and Boyle et al (1988), where the homologous recombination arms flanking the CHIKV-26S and Ecogpt expression cassettes were designed to be homologous with the sequences flanking the A39R ORF. Briefly, homologous recombination was carried out in BHK21 cells that were infected at a moi of 0.01 pfu/cell for 1 hour with VACV-COP followed by transfection with the CHIKV-26S homologous recombination cassette. The infected/transfected cells were then incubated for 2 to 3 days until gross cytopathic effects could be seen followed by harvesting and cell lysis to make a viral extract. SCV301C was positively selected for by Ecogpt drug selection using MXHAT treatment of BHK21 cells as described in Protocol 6 of Smith (1993), except 20 rounds of plaque purification by limited dilution in 48WP was carried out to eliminate traces of parental VACV-COP as assessed by A39R specific PCR analysis. A candidate clone was then amplified in BHK21 cells without MXHAT treatment to make a virus seed stock from which batches of SCV301C for vaccination studies was derived. The sequence of the SCV301C genome is given in SEQ ID NO:3.

REFERENCES

Chakrabarti, S, Sisler, J R, and Moss, B (1997). Compact, synthetic, vaccinia virus early/late promoter for protein expression. Biotechniques 23: 1094-1097.

TABLE 1

SCV301C homologous Recombination Cassette Feature Table

| Element | Description | Size |
|---|---|---|
| A39R-F1 arm | Homologous recombination arm 1 targeting up-stream of the A39R ORF | 501 bp |
| prPs | Early/late vaccinia virus promoter | 44 bp |
| EGFP | Protein coding sequence of Enhance Fluorescent Green Protein | 720 bp |
| T5NT | Vaccinia virus early transcriptional stop sequence | 7 bp |
| prPs | Early/late vaccinia virus promoter | 44 bp |
| Ecogpt | *E. coli* guanine phosphoribosyl transferase protein coding sequence | 459 bp |
| T5NT | Vaccinia virus early transcriptional stop sequence | 7 bp |
| prPs | Early/late vaccinia virus promoter | 44 bp |
| CHIKV 26S | Protein coding sequences of CHIKV 26S polyprotein consisting of Capsid, E3, E2, gp6K and E1. Sequence derived from Genbank accession number: AM258992. | 3747 bp |
| T5NT | Vaccinia virus early transcriptional stop sequence | 7 bp |
| A39R-F2 arm | Homologous recombination arm 2 targeting down-stream of the A39R ORF | 501 bp |

SCV301A was constructed by insertion of the CHIKV-26S homologous recombination cassette into vaccinia virus Copenhagen strain (VACV-COP) by replacing the A39R ORF via homologous recombination between the F1 and F2 with their homologous sequences with the VACV-COP genome as shown in FIG. 2 above that results in the insertion configuration shown in FIG. 3.
Methodology
SCV301C (VACV-CHIKV) was constructed by homologous recombination to replace the A39R ORF of VACV with the CHIKV-26S homologous recombination cassette that was synthesized by GeneArt GmbH consisting poxvirus expression cassette expressing the CHIKV 26S-structural Smith, G L (1993) In: Davison, A J and Elliotand, R M (eds). *Expression of genes by vaccinia virus vectors in "Molecular Virology a Practical Approach"*. IRL Press at Oxford University Press.

Falkner, F G, and Moss, B (1988). Escherichia coli gpt gene provides dominant selection for vaccinia virus open reading frame expression vectors. J Virol 62: 1849-1854.

Boyle, D B, and Coupar, B E (1988). A dominant selectable marker for the construction of recombinant poxviruses. Gene 65: 123-128.

Construction of SCV305 (SCV-CHIK)
Deletion of EGFP/Ecogpt Reporter Cassette to Create SCV302

Description

In order to construct SCV305, the EGFP and Ecogpt expression cassettes need to be deleted from SCV301C to create SCV302 a recombinant vaccinia virus Copenhagen strain that contains solely the Chikungunya 26S polyprotein expression cassette inserted into the A39R ORF. This virus was constructed by deleting the Ecogpt/EGFP reporter expression cassettes from SCV301C by homologous recombination with pTC29 and counter selecting for viruses with functional Ecogpt expression as shown below in FIG. 4.

Description of pTC29 pTC29 is a plasmid clone that contains the homologous recombination arms, A39R-F1 and SCV301C-F2, required for the deletion of the EGFP and Ecogpt expression cassettes from SCV301C by homologous recombination as shown in FIG. 4. The sequence details of pTC29 are given in SEQ ID NO:4 and a plasmid map is shown in FIG. 5.

Methodology

The Ecogpt and EGFP expression cassettes were removed from SCV301C by a homologous recombination and counter selection against Ecogpt expression as described in protocol 7 of Smith (1993) and published in Isaacs et al (1990) whereby the homologous recombination arms were designed to be homologous to the sequences flanking the Ecogpt and EGFP expression cassettes within the recombinant VACV-CHIK genome. After homologous recombination, SCV302 was further plaque purified in an hrpt$^-$ cell line in the presence of 6-thioguanine (6-TG) to counter select against contaminating virus expressing Ecogpt, i.e., the original SCV301C.

REFERENCES

Smith, G. L. (1993). Expression of genes by vaccinia virus vectors. In Molecular Virology a Practical Approach, A. J. Davison and R. M. Elliotand, eds. (IRL Press at Oxford University Press), pp. 257-283.

Isaacs, S. N., Kotwal, G. J., and Moss, B. (1990). Reverse guanine phosphoribosyltransferase selection of recombinant vaccinia viruses. Virology 178, 626-630.

Deletion of B7R-B8R and D13L to Create SCV305

Description

SCV305 was constructed by simultaneously removing the D13L and B7R-B8R ORFs from SCV302 in a single homologous recombination reaction with D13L Deletion Homologous Recombination (HR) cassette (deletion of D13L with transdominant CP77/DsRed selection) and B7R-B8R Deletion Homologous Recombination (HR) cassette (deletion of B7R-B8R with Cyan/Zeocin transdominant selection). Detail of the configuration of each cassette are shown in FIGS. 6 and 7 and sequence detail are given in SEQ ID NO:5 and SEQ ID NO:6.

TABLE 2

D13L Deletion HR Cassette Feature Table

| Element | Description | Size |
|---|---|---|
| D13L-F1 | D13L-F1 deletion homologous recombination arm | 1000 bp |
| prCP77 | CPXV-BR A25L promoter (early promoter) | 136 bp |
| CP77 | Cowpox CHO host range protein (BR-A25L ORF) | 2007 bp |
| T5NT | Vaccinia virus early transcriptional stop sequence | 7 bp |
| prPs | Vaccinia virus early/late promoter | 44 bp |
| DsRed | DsRed-Express2 protein coding sequence | 678 bp |
| T5NT | Vaccinia virus early transcriptional stop sequence | 7 bp |
| F1-Rpt | 3' repeat sequence of D13L-F1 arm | 251 bp |
| D13L-F2 | D13L-F2 deletion homologous recombination arm | 1000 bp |

TABLE 3

B7R-B8R Deletion HR Cassette Feature Table

| Element | Description | Size |
|---|---|---|
| B7R-F1 | D7R-F1 deletion homologous recombination arm | 1000 bp |
| prPs | Vaccinia virus early/late promoter | 40 bp |
| AmCyanZeo | AmCyan flourescent protein fusion with Zeocin resistance protein coding sequence | 1059 bp |
| T5NT | Vaccinia virus early transcriptional stop sequence | 7 bp |
| F1-Rpt | 3' repeat sequence of B7R-F1 arm | 305 bp |
| B8R-F2 | B8R-F2 deletion homologous recombination arm | 1000 bp |

In order to select for virus with a D13L deletion, cell lines expressing D13 protein were used: CHO+D13 (CHO cell line expressing D13 protein) and CHO+D13+CP77 (CHO cell line expressing D13 protein and CP77 protein). The reason for employing two such cell lines is that CP77 expression by virus enables propagation in CHO cells and was therefore used as a positive selection tool. Replacement of the D13L ORF with the CP77/DsRed expression cassette enables amplification of D13L deleted virus in CHO-D13 cells that can be verified by red fluorescence of infected cells. In order to delete the CP77/DsRed reporter cassette after D13L deletion was confirmed, intramolecular recombination was designed to delete this cassette when viral expression of CP77 was no longer required. This was done by amplifying the D13L deleted virus in CHO+D13+CP77 that not only expresses the D13 protein but also the CP77 protein making viral expressed CP77 redundant and allowing its removal by intramolecular recombination as exemplified in FIG. 4.

In order to select for virus with B7R-B8R deletion, a Zeocin resistance/Cyan fluorescent reporter cassette was used to replace these ORFs by homologous recombination. Insertion of Zeocin/Cyan cassette was positively selected for by culturing the cells in Zeocin during infection and selecting for cyan fluorescent cells. Once the deletion of B7R-B8R was confirmed the removal of this reporter by intramolecular recombination was initiated in the absence of zeocin during infection as exemplified in FIG. 8.

The experimental strategy to simultaneously delete D13L and B7R-B8R was done by (i) homologous recombination of SCV302 with D13L Deletion HR cassette and B7R-B8R HR cassette in CHO+D13 cells, (iii) amplifying SCV305 in CHO+D13 cells treated with Zeocin, (iii) isolating individually infected cells that co-fluoresced cyan and red until a pure double knockout clone was isolated, and then (iv) initiating removal of both reporter cassettes by infecting CHO+D13+CP77 cells without zeocin treatment and isolating non-fluorescent (with respected to cyan and red) infected cells.

Clones identified as being free from contaminating virus intermediates with the target ORFs deleted were confirmed by PCR and sequencing analysis. The presence of the CHIKV-26S expression cassette within the A39R ORF was further confirmed by PCR and sequencing analysis and expression of CHIKV proteins confirmed by western blot analysis. Total attenuation of SCV305 was verified by an infectivity study in vaccinia virus permissive cell lines.

Methodology

Both D13 Deletion HR and B7R-B8R Deletion HR cassettes were synthesized by GeneArt GmbH. To generate SCV305 (SCV-CHIK), the D13L ORF and B7R-B8R ORFs were deleted from SCV302 by homologous recombination, in which positive selection for successful deletions was undertaken by infection of CHO cells expressing only the D13 protein (CHO-D13) in the presence of Zeocin. Because CHO is nonpermissive to VACV infection, positive selection for D13L-deleted virus was achieved by replacing the D13L ORF with an expression cassette coding for the cowpox virus CHO host-range protein CP77. A homologous recombination plasmid was constructed that consisted of a CP77 expression cassette and a dsRed fluorescent protein expression cassette flanked by left and right recombination arms that were homologous to sequences flanking the D13L ORF within SCV302. The dsRed expression cassette was added, because VACV-expressing CP77 does not form lytic plaques in CHO; therefore, infection was monitored by the presence of red fluorescence. To help in removal of the CP77 and dsRed expression cassettes that had replaced the D13L ORF and the AmCyanZeo expression cassette that replaced the B7R-B8R ORFs, a repeat sequence of the left homologous recombination arm was placed downstream of the CP77 and dsRed expression cassettes and the downstream of the AmCyanZeo expression cassette but upstream of the right homologous recombination arm within both homologous recombination cassette. Homologous recombination was performed by transfecting the D13L and B7R-B8R-deleting homologous recombination cassettes into CHO-D13 previously infected with VACV-CHIK at an MOI of 0.01 PFU/cell. SCV305 was enriched from the homologous recombination infection by amplifying the virus in CHO-D13 treated with Zeocin, followed by infecting a fresh set of CHO-D13 cells treated with Zeocin with the amplified virus. These infected cells were recovered and made into a single-cell suspension by TrypLE Select digestion (Thermo Fisher Scientific) and then single-cell sorted so that one red and cyan fluorescent cell was seeded into 1 well of a 96-well plate containing cultured CHO-D13 cells treated with Zeocin using a FACSAria Fusion flow cytometer (BD Biosciences). The red/cyan fluorescent cell-seeded 96-well plate was then incubated at 37° C./5% CO2 until red and cyan fluorescent foci of infection could be seen in any of the wells of the 96-well plate. Wells containing a single focus of infection were harvested and resuspended as single-cell suspensions before single-cell sorting and seeding into 96-well plates of fresh CHO-D13 cells treated with Zeocin. This single-cell sorting process was repeated five times to eliminate trace contamination with the original SCV302 and produce clonal SCV305. A number of clonally purified SCV305 candidates were amplified in CHO-D13 treated with Zeocin cells and then tested by PCR analysis for the presence of contaminating SCV302 and to confirm D13L replacement by the CP77 and dsRed expression cassettes and replacement of the B7R-B8R with AmCyanZeo expression cassette. The best clone was then amplified in the CHO+D13+CP77 line (expressing both CP77 and D13 proteins) to encourage intramolecular recombination between the left homologous recombination sequences and the repeat sequences, because the dependence of the viral expression of CP77 is no longer required and the need for the Zeocin resistance protein expression is nolonger required in the absence of Zeocin, resulting in the deletion of the CP77 and dsRed expression cassettes and the AmCyanZeo expression cassette from SCV305. The infected CHO+D13+CP77 cells were brought into single-cell suspension by digestion with TrypLE Select and cell sorted using a FACSAria Fusion flow cytometer, in which non-fluorescent cells were bulk sorted and retained. SCV305 virus was further amplified to make seed stock by progressive scaled-up infections of CHO+D13+CP77 cells. The entire genomic sequence of SCV305 is given in SEQ ID NO:7.

Construction of SCV1002 (SCV-CHIK/ZIKA)

Description

SCV1002 is a single vectored multivalent Chikungunya and Zika virus vaccine which consist of the following features:

Replacement of the A39R ORF with an SCV-CHIKV-26S-subgenomic expression cassette (CHIKV-26S)

Replacement of the B7R-B8R ORFs with SCV-ZIKV-prME expression cassette

Deletion of the D13 ORF

SCV1002 was constructed by replacing the B7R-B8R ORFs of SCV302 with a Zika Virus prME polyprotein expression casstte and deleting the D13L ORF. The sequence details of the the Zika virus prME expression cassette is given in SEQ ID NO:8 where the origin of the prME sequence was taken from the Brazilian strain ZikaSPH2015 (Genbank: KU321639). A ZIKV-prME homologous recombination (HR) cassette was synthesized by GeneArt as shown in FIG. 10 where the sequence details are given in SEQ ID NO:9.

TABLE 4

ZIKV prME HR Cassette Feature Table

| Element | Description | Size |
| --- | --- | --- |
| B7-F1 arm | Homologous recombination arm flanking the B7R ORF | 1000 bp |
| T5NT | Poxvirus early transcriptional stop sequence of the BFPzeo expression cassette | 7bp |
| BFPzeo | Protein coding sequence for the Blue Fluorescent Protein and Zeocin inactivating enzyme fusion protein | 1071 bp |
| prPs | Vaccinia virus early/late promoter of the BFPzeo expression cassette | 40 bp |
| F1-Rpt arm | F1 arm repeat sequence | 301 bp |
| prPs | Vaccinia virus early/late promoter | 40 bp |
| prME polyprotein | Protein coding sequence of the prME polyprotein sequence. The sequence was derived from Genbank: KU321639 (Brazilian strain ZikaSPH2015) | 2076 bp |

TABLE 4-continued

ZIKV prME HR Cassette Feature Table

| Element | Description | Size |
| --- | --- | --- |
| T5NT | Poxvirus early transcriptional stop sequence of the ZIKV-PrME expression cassette | 7 bp |
| B8-F2 arm | Homologous recombination arm flanking the B8R ORF | 1000 bp |

Methodology

SCV1002 (SCV-CHIK/ZIKA) was constructed by replacing the B7R-B8R ORF with a poxvirus expression cassette for ZIKV prME (Brazilian isolate ZikaSPH2015, Genbank: KU321639) and deleting the D13L ORF by homologous recombination. For insertion of the ZIKV prME expression cassette by replacing the B7R-B8R ORFs a homologous recombination cassette was synthesize by GeneArt GmbH consisting of the following elements: (i) F1 homologous recombination targeting sequences upstream of the B7R gene, (ii) an expression cassette consisting of a vaccinia virus early/late promoter operatively linked to a protein coding sequence for a fluorescent blue protein fusion with Zeocin resistance protein (BFPzeo) and ending with a poxvirus early transcriptional stop sequence, (iii) a repeat of the F1 homologous recombination arm, (iv) an expression cassette consisting of a vaccinia virus early/late promoter operatively linked to a protein coding sequence for ZIKV prME followed by a poxvirus early transcriptional stop sequence and finally (v) F2 homologous recombination targeting sequences downstream of the B8R gene. The D13L ORF was removed as described in the construction of SCV305 (SCV-CHIK).

Homologous recombination was performed by transfecting both the ZIKV prME HR cassette and D13L deletion HR into CHO+D13 cells previously infected with SCV302 at an MOI of 0.01 PFU/cell. The resulting SCV1002 was enriched from the homologous recombination infection by amplifying the virus in CHO+D13 cells in the presence of Zeocin (ThermoFisher Scientific) followed by a second infection of a fresh set of CHO+D13 cells in the presence of Zeocin with amplified virus. These infected cells where recovered and made into a single cell suspension by TrypLE Select digestion and then single cell sorted so that a single blue and red fluorescent cell was seeded into one well of a 96 well plate containing CHO+D13 cells using FACSAria Fusion flow cytometer (BD Biosciences). After incubation in the presence of Zeocin, wells containing a single blue and red fluorescent focus of infection where harvested and resuspended as single cell suspensions before single cell sorting and seeding into 96 well plates of fresh CHO+D13 cells. This single cell sorting and culturing in the presence of Zeocin was repeated five times to eliminated trace contamination with the original SCV302 and produce clonal SCV1002. Several clonally purified SCV1002 were amplified in CHO+D13+CP77 cells in the absence of Zeocin and were then subject to PCR analysis to confirm insertion of ZIKV prME into the B7R-B8R locus, retention of the CHIK expression cassette in the A39R locus, and absence of contaminating SCV302. Clones were amplified in CHO+D13+CP77 cells in the absence of Zeocin to encourage intramolecular recombination between the F1 homologous recombination sequence and the F1 repeat sequence resulting in the deletion of both BFPzeo and DsRed/CP77 expression cassettes. Single cell suspensions of these cultures were bulk sorted (FACSAria) and non-fluorescent cells retained. The PCR was repeated to confirm retention of inserts and loss of BFPzeo, DsRed/CP77 and deletion of the D13L ORF. SCV1002 vaccine stocks were prepared in CHO-D13+CP77 cells and titred. The sequence of the entire SCV1002 genome is given in SEQ ID NO:10.

Example 2

Vaccinations with SCV305 Protects Against ECTV

Groups of 6-8 week old female C57BL/6 mice (n=5 mice per group) were vaccinated i.p. with SCV305 ($10^5$, $10^6$, $10^7$ PFU) or sham vaccinated with PBS. Anti vaccinia virus-specific IgG levels determined by end-point ELISA. Vaccination with SC305 was seen to provide substantial specific anti-vaccinia viral antibody titres which were similar to that achieved with vaccination of a similar dose vaccinia virus (VACV).

After four weeks, mice were challenged with a lethal dose (50 $LD_{50}$) of mousepox virus, Ectromalia (ECTV). ECTV is highly infectious to mice and causes the same symptoms in mice as smallpox causes in humans.

Mice vaccinated with $10^7$, $10^6$, and $10^5$ PFU SCV305 or $10^5$ PFU VACV exhibited similar levels of protection against weight loss, clinical symptoms, and mortality. Dissemination of ECTV to multiple organs was also prevented in all vaccinated mice. These results illustrate that a single vaccination with SCV305 provides complete protection from a lethal poxvirus challenge, suggesting that the SCV retains utility as a smallpox vaccine.

A Single Vaccination with SCV305 Produces Robust and Durable Anti-Chikungunya Virus Antibody Responses Antibodies are deemed to be critical for protection against chickungunya virus (CHIKV), with human and mouse antibodies directed at the E2 surface glycoprotein of CHIKV shown to mediate protection. Mice were given a single dose of vaccine ($10^5$, $10^6$ and $10^7$ PFU of SCV-CHIK) and CHIKV E2-specific IgG responses were examined by ELISA. A dose and time dependent increase in CHIKV-E2 specific IgG levels was observed, with mice given $10^7$ PFU showing similar kinetics and magnitude of antibody responses to that induced by replication-competent VACV-CHIK vaccinated mice. This illustrated that the multiplication-defective SCV305 vaccine was able to generate comparable antibody responses to a recombinant immunogen as the multiplication-competent VACV-CHIK vaccine.

Neutralizing antibody responses were detected in 4/6 mice receiving $10^5$ PFU of the SCV305 vaccine, whereas all 6 mice receiving $10^6$ PFU and $10^7$ PFU of the SCV305 vaccine generated neutralizing antibody responses.

CHIKV-specific IgG1 and IgG2c levels were examined in serum of mice day 30 post-vaccination to provide an indication of the 'Th1/Th2 balance' of the antibody responses. At $10^7$ PFU, SCV305 stimulated IgG2c responses comparable to those induced by VACV-CHIK. However, SCV305 induced higher IgG1 responses than VACV-CHIK, suggesting the generation of a more balanced Th1 (IgG2c)/Th2 (IgG1) response by SCV-CHIK, with VACV-CHIK being more Th1 biased.

To analyze the longevity of antibody responses induced by the SCV-CHIK vaccine, anti-CHIKV antibody responses were examined at 4 weeks, 6 months and 1 year post-vaccination. A limited drop in anti-CHIKV antibody levels was observed over this time period, with antibody levels remaining comparable between SCV305 and VACV-CHIK vaccinated mice throughout. In addition, CHIKV E2-specific antibody secreting cells (ASC) and CHIKV E2/E1 and capsid specific IFN-γ producing cells were detected at 1 year post-vaccination in SCV305 and VACV-CHIK vaccinated mice.

The vaccination-CHIKV challenge model was piloted by demonstrating that mice vaccinated with VACV-CHIK ($10^7$ PFU) and challenged with CHIKV (Reunion Island isolate; LR2006-OPY1, $10^4$ $CCID_{50}$) were completely protected against viraemia and arthralgia. Since the SCV-CHIK vaccine induced neutralizing antibody responses comparable to VACV-CHIK at the same $10^7$ PFU dose, the protective efficacy of the SCV305 vaccine was evaluated at lower doses ($10^5$ and $10^6$ PFU). Mice vaccinated with SCV305 at $10^6$ PFU and challenged 40 days later (with the Reunion Island isolate; LR2006-OPY1, $10^4$ $CCID_{50}$) showed no detectable viraemia or foot swelling. Mice vaccinated with a 10-fold lower dose ($10^5$ PFU) were partially protected, with an approximate 4-log reduction in viraemia and significantly reduced foot swelling compared to control VACV-infected mice. Longevity studies confirmed that SCV305 vaccinated mice were protected against CHIKV challenge one-year post-vaccination.

Persistence of CHIKV genomic RNA, particularly in the joint tissues, has been associated with chronic arthritic disease following CHIKV infection in humans and in the mouse model. At 30 days post-challenge, mice vaccinated with $10^6$ PFU of the SCV305 vaccine, showed a significant reduction to background levels in the level of persistent viral RNA, illustrating that SCV305 vaccination can prevent establishment of persistent CHIKV RNA in joint tissues.

Taken together, these findings demonstrate the ability of the SCV305 vaccine to elicit a robust, balanced, and durable CHIKV-specific antibody response, and provide protection against viraemia, acute arthritis, and persistence of viral RNA following CHIKV challenge.

Example 3

SCV1002 Vaccinations

When combining different live attenuated viral vaccines, competition between the viruses is the most frequently observed problem. It can be circumvented by increasing the dose of the combination vaccine or adjusting the dosage of each vaccine component to overcome competition from the dominant vaccine(s) components.

Antigenic competition by 'immunological interference' has been reported between components of the trivalent diphtheria-pertussis-tetanus vaccine, between canine distemper bacterins and live canine distemper virus and when Bordatella is used as a diluent for live combination distemper virus, adenovirus type 2, parvovirus and parainfluenza virus vaccines (Hunt et al, 2001). In these examples, inoculation with the multicomponent vaccine elicits less antibody than when the components are administered alone. In some cases the response to one antigen dominates while the responses to the others are suppressed. In other cases, where mutual competition occurs, the response to all components is reduced.

The degree of antigenic competition has been shown to be dependent on a number of parameters of vaccination, including the relative sites of inoculation of the competing antigens, the time interval between administration of the antigens and the dose of the dominant antigen relative to the suppressed antigen.

Even though the above can be solved by expressing the immunizing antigens from several disease causing agent from the same vector, thereby ensuring equal representation of each immunizing antigen to the immune system and with a single vector for antigen delivery only the optimal route of vaccination for the vector only needs to be considered, there is the risk that antigen interference can occur by preferential antigen capture and MHC presentation by antigen presenting cells such as B cells and dendritic cells. An antigen with dominant B cell and or T cell epitopes will produce a stronger immune response than an antigen that have sub-optimal B-cell and or T-cell epitopes. Therefore this would lead to a biased immune response to the most dominant antigen when vaccinated with a single vector that expresses multiple antigens from multiple disease causing agents. It would be expected that an antigen expressed from a vector that also expresses other antigens from other diseases, eg, chikunyunga antigen expressed along with Zika virus antigens, may not produce as strong an immunizing response than an immunizing vector that only expresses the chikungunya antigen.

A study was carried out to determine if the expression of multiple dominant antigens from multiple disease causing virus will interfere with each other's immune response. For example chikungunya E2 protein is very potent at stimulating a very good neutralizing antibody response that can neutralize chikungunya infection. Likewise, Zika virus E protein also stimulates a potent neutralizing antibody response to neutralize Zika virus infection. However, expressing these two dominant antigens from the same vector may interfere with each others capacity to stimulate a potent immune response to their respective viruses, ie, one dominant antigen may have more dominance over the other.

To determine if expressing multiple dominant antigens from the same vector is not detrimental in stimulating optimal immune responses as compared to expressing each dominant antigen from a single vector, a vaccination study in mice was carried out comparing SCV1002 (CHIK/ZIKA vaccine) with SCV305 (CHIK vaccine) with respect to stimulation of chikungunya specific neutralization antibodies.

Vaccination Strategy:

Wildtype C57BL/6 and interferon receptor deficient mice (IFNAR) females mice were vaccinated once with either the single-vectored CHIKV/ZIKV vaccine (SCV1002), CHIKV only (SCV305) or empty vector control (SCV105) in groups of 6 mice per treatment group. All treatment groups were given $10^6$ pfu/mouse of vaccine via intraperitoneal injections and bled at 2 and 4 weeks post-vaccination. All mice were challenged at 6 weeks post-vaccination.

Neutralization Assay:

Levels of neutralising antibodies are often used as correlate of protection. Therefore levels of neutralising antibodies was calculated prior to challenge in all vaccine groups, ZIKV/CHIKV (SCV1002), CHIKV only (SCV305) or empty vector control (SCV105) using a standard microneutralisation assay on Vero cells against the Reunion strain of chikungunya. In brief, sera was heat inactivated (56° C. for 30 min) serum from each mouse was serial diluted in duplicate in 96 well plates and incubated with 100 $CCID_{50}$ units of virus and incubating for 1 hr at 37° C. Following this neutralisation step, freshly split Vero cells were overlaid ($10^4$ cells per well) onto the serum/virus mixture and incubated for 5 days until cytopathic effects were visualised under a microscope. The serum dilution giving 100% protection against cytopathic effect was determined using crystal violet staining.

Results

Both vaccine candidates expressing CHIKV antigens did induce neutralising antibodies against chikungunya virus after a single administration of vaccine.

However, a single administration of the single-vectored CHIK/ZIKA vaccine induce much higher levels of CHIKV neutralising antibodies despite equivalent doses used for vaccination.

Conclusion

This vaccination study showed that when mice were vaccinated with a single shot of an equivalent doses of SCV305 (CHIK only vaccine) and SCV1002 (single-vectored CHIK/ZIKA vaccine) the single-vectored vaccine (SCV1002) gave better chikungunya specific neutralising antibody responses. This was unexpected as it was perceived that expression of the other dominant antigen, ie, the Zika virus E protein would compete for immune responses and thus dampen or even-out the immune response to both dominant antigens of Chikungunya (E2 antigen the target for neutralizing antibodies) and Zika virus (E antigen the target neutralizing antibodies). This does not seem to be the case and it can be speculated that expression of the Zika virus antigen had an adjuvant effect to help increase the immune response the chikungunya antigens that are expected to for chikungunya VLPs upon vaccination.

Protection of Mice Foetuses from Zika Virus Infection of Mothers that had Previously been Vaccinated with SCV1002 Before Pregnancy The major complications of an ongoing Zika virus outbreak in the Americas and Asia are congenital defects caused by the virus's ability to cross the placenta and infect the fetal brain. Setoh et al (2017, *De Novo Generation and Characterization of New Zika Virus Isolate Using Sequence Data from a Microcephaly Case. mSphere* 2:e00190-17. https://doi.org/10.1128/mSphereDirect.00190-17) describes a mouse model where ZIKV-Natal strain could be used to establish a fetal brain infection model in IFNAR −/− mice (including intrauterine growth restriction) without causing symptomatic infections in dams.

The aim of this study was to show that previous vaccination of female mice with SCV1002 (single-vectored ZIKA/CHIK) prior to pregnancy can afford protection against Zika virus infection of their unborn foetuses.

This study was carried out by vaccinating female IFNAR −/− with either SCV1002 (single-vectored CHIK/ZIKA vaccine) or SCV105 (vector only) followed by mating with male IFNAR mice. Pregnant mice were then infected with Zika virus-natal strain as described by Setoh et al (2017).

Vaccination Schedule:

Six-eight week female interferon receptor deficient mice (IFNAR −/−) were vaccinated once via the intramuscular route with either the single-vectored vaccine, ZIKV/CHIKV (SCV1002) or the empty control vaccine (SCV105) at week 0 at $10^6$ per mouse Groups of mice were bled at 4 weeks post-vaccination to check for seroconversion to the vaccine At 6 weeks post-vaccination, timed matings were initiated to induce pregnancy in vaccinated mice. Female mice were checked daily for evidence of successful pregnancy (vaginal plugs)

As embryonic day 6.5, pregnant mice were infected with Zika Natal strain at $10^4$ CCID50 units via subcutaneous infection Following infection, pregnant mice were bled daily between days 1 to 5 to check for viraemia At embryonic day 17.5, pregnant mice were culled, maternal placenta and foetal heads harvested to assess for infectious ZIKV as described by Setoh et al (2017).

Results

Pregnant female mice previously vaccinated with SCV1002 (CHIK/ZIKA vaccine) prior to becoming pregnant was able to prevent Zika virus replication during challenge with Zika virus Natal strain as shown by no detection of viraemia post-challenge. However, as expected the SCV105 (SCV vector only) vaccinated mice were not able to prevent viral replication with Zika virus as shown by the high level of viraemia seen in the first 5 days after challenge.

Female mice that were previously vaccinated with a single shot of SCV1002 (CHIK/ZIKA vaccine) prior to mating and pregnancy showed no detectable levels of Zika virus after challenge in their placentas and in the brains of foetuses. Vaccination prevent challenge virus infecting the placenta and by doing so blocked onward transmission of Zika virus to the vulnerable foetuses.

However, this was not the case for female mice previously vaccination with SCV vector only where after challenge during pregnancy some of the placentas became infected and transmission of Zika virus infections to some of the brains of the foetuses had occurred.

Conclusions

Pregnant female mice previously vaccinated with a single shot of CHIK/ZIKA single vectored vaccine were protected from a ZIKV challenge compared to the control vaccine as shown by the viraemia results.

Vaccination of the mothers prior to pregnancy afforded protection their the unborn foetuses by preventing the Zika virus challenge virus infecting the maternal placenta and blocking onwards transmission to fetal brain.

These results demonstrate in this preclinical model that onwards transmission of the Zika challenge virus to the foetus can be blocked by prior vaccination of mother before pregnancy.

SCV1002 Affords Protection to Mice From a Lethal Challenge with Ross River Virus Chikungunya (CHIKV) belongs to the Alphaviruses group where another member of that group is Ross River Virus (RRV). RRV, is endemic in the northern and central parts of Australia as well as in the Pacific regions. RRV and CHIKV are transmitted by mosquitoes and can both cause polyarthritis and lead to persistent infections in humans. However, the mosquito vectors for chikungunya virus are *Aedes aegypti* and *Aedes albopictus* whereas the main mosquito vectors for Ross River Virus are two salt marshbreeding mosquitoes *Aedes camptorhynchus* and *Aedes vigilax* and the fresh water breeding mosquito *Culex annulirostris*.

A vaccination study in a strain of mice (IRF3/7 knockout) that is lethally susceptible to RRV was performed to determine if the chikungunya vaccine antigens of SCV1002 could afford full protection against a lethal challenge with RRV six weeks post vaccination with SCV1002 (CHIK/ZIKA vaccine).

Experimental Design

This vaccination and challenge study was performed in IRF3/7 knockout mice that are susceptible to both chikungunya and Ross River virus infects where infection with these viruses are lethal in this mouse strain.

Two groups of IRF3/7$^{-/-}$ mice where either vaccination with a single shot of $10^6$ pfu per mouse of SCV1002

(single-vectored CHIK/ZIKA vaccine) or SCV105 (SCV vector only) via intramuscular route.

At 6 weeks post vaccination all mice were challenge with $10^4$ $CCID_{50}$ of Ross River Virus (strain TT) via subcutaneous route into the top of the feet as described by Rudd et al (2012).

Survival from challenge was monitored for 30 days post-challenge. Mice were euthanised when clinical symptoms reached ethically defined end points (as described in Rudd et al (2012) *Interferon Response Factors 3 and 7 Protect against Chikungunya Virus Hemorrhagic Fever and Shock. J. Virol.*, 86 (18): 9888-9898)).

Results

Vaccination of $IRF3/7^{-/-}$ with SCV1002 but not SCV105 was found to provide full protection from lethal of RRV challenge. This demonstrates that SCV-CHIK/ZIKV vaccine (SCV1002) is cross protective to other viruses in the Alphavirus genus.

SCV1002 Vaccinated $IFNAR^{-/-}$ Mice Challenged with ZIKV then CHIKV

Groups of 6 adult female mice>6 weeks of age were injected with $10^6$ pfu/mouse of SCV1002, SCZ305 or SCV105 (SCV empty vector) via intraperitoneal injection. Mice were monitored for any adverse effects following vaccination.

Six weeks post-vaccination, groups of mice were challenged with $10^3$ $CCID_{50}$/mouse of mouse adapted African Zika strain MR766 via subcutaneous injection into the base of the tail.

Six weeks post-Zika virus challenge, surviving groups of mice were challenged with $10^4$ $CCID_{50}$/mouse of the La Reunion strain of chikungunya virus (LR2006-OPY1) via subcutaneous injection into the top of the foot.

Results

SCV1002 (single vectored CHIK+ZIK vaccine) vaccinated mice were fully protected from Zika virus challenge however SCV305 (CHIK only vaccine) and SCV105 (vector only) vaccinated mice all succumbed to Zika virus infection by day 9 post infection.

SCV1002 (single vectored CHIK+ZIK vaccine) vaccinated $IFNAR^{-/-}$ mice that were first challenged with ZIKV and survived where partially protected, ie, 33% efficacious, against an extremely lethal challenge with CHIKV that was able kill all unvaccinated mice by day 3 post challenging.

Conclusions

SCV1002 vaccination of $INFAR^{-/-}$ mice with a single dose at $10^6$ pfu/mouse afforded full protection against a lethal challenge with a mouse adapted strain of Zika virus.

Subsequent challenge of surviving mice with an extremely lethal dose of CHIKV were partially protected, ie, the SCV1002 vaccine was 33% efficacious in this mouse model for CHIKV infection at $10^4$ infectious units per mouse. The challenging dose of $10^4$ infectious was too high for this immune compromised mouse model that lack the Interferon receptors and so were unable to respond to interferon in an antiviral mode. Production of antiviral interferons would normally control the initial infection while the adaptive immune response has time to react to the invading viral infection. In hind sight this dose for CHIKV challenging in this mouse model was too high as it killed all non-vaccinated mice within 3 days—too short a time frame for antiviral anamnestic antibody response to occur in order to control and clear the invading viral infection. In the natural situation antiviral interferons would control the initial viral infection long enough for the adaptive immune response to take over and neutralize and clear the infection from the host. Despite the un-naturally high level of virulence of CHIKV in IFNAR mice, where unvaccinated mice were killed by day 3 post infection with a dose of $10^4$ infectious units, vaccination with SCV1002 was unexpectedly able to afford some protection under this extreme condition thus highlighting the high immunogenic potency of this vaccine.

CHIKV Infection Followed by SCV1002 Vaccination

The aim of this study was to evaluate antigen interference or antigenic sin in the context of natural infection. Would a previous natural infection with chikungunya virus affect the induction of an immune responses to Zika virus while vaccine induced boosting responses to chikungunya is occuring following vaccination with SCV1002 (SCV-CHIK/ZIKA vaccine).

Wildtype C57BL/6 mice were infected with chikungunya virus, allowed to clear the virus and then boosted with the single vectored CHIKV/ZIKV vaccine. Mice were bled prior to vaccine boost and 4 weeks after vaccination to assess levels of anti-CHIKV and anti-ZIKV antibodies responses.

Groups of 6 adult female mice >6 weeks of age were injected with $10^4$ $CCID_{50}$/mouse of the La Reunion strain of chikungunya virus (LR2006-OPY1) via subcutaneous infection into the top of the foot. Mice were monitored for any adverse effects following infection and were bled at 8 weeks following infection, prior to vaccination Eight weeks post-infection, mice were boosted with single-vectored CHIKV/ZIKV vaccine (SCV1002) with $10^6$ pfu/mouse delivered intraperitoneally. Mice were monitored for any adverse effects following vaccination and four weeks after vaccination, mice were bled again to compare levels of anti-CHIKV and anti-ZIKV antibodies before and after vaccination.

SCV1002 vaccination of wildtype mice previously exposed to CHIKV infection was found to induce anti-ZIKV antibodies to similar levels seen previously without CHIKV infection.

Antigenic sin is a phenomenon whereby exposure to one antigen can inhibit the ability of a second antigen to induce a protective immune response. The mechanism behind this concept is suggested to involve B cells primed to the first antigen which are programmed to respond only to the first antigen. When a second antigen is introduced these B cells essentially remove the second antigen before a productive immune response can be generate, leading to very low or poor immunity. This concept was tested in this study.

However, as mice previously infected with chikungunya virus and then vaccinated with CHIKV/ZIKV vaccine were able to induce a productive CHIKV and ZIKV immune responses similar to that seen without prior CHIKV infection, antigenic sin is not in play in this setting. This is most likely because CHIKV and ZIKV are very different viruses coming from two distinct virus families. This data would suggest that the dual vaccine could be used in countries with known prior circulation of CHIKV.

Protection Against ZIKA Virus Infection in Male Mice

Zika virus remains the only mosquito-transmitted virus that can also be transmitted sexually Zika virus can be transmitted from male-to-female or male-to-male and the virus has been shown to persist in semen for up to several months after the onset of symptoms.

The aim of this study was to show that vaccination with SCV1002 (single-vectored ZIKA/CHIK) could afford protection against Zika virus infection in male mice.

This study was carried out by vaccinating male IFNAR −/− with either SCV1002 (single-vectored CHIK/ZIKA vaccine) or SCV105 (vector only) followed by infection with Zika virus-natal strain as described by Setoh et al (2017) (De Novo Generation and Characterization of New Zika Virus Isolate Using Sequence Data from a Microcephaly Case. mSphere 2:e00190-17. https://doi.org/10.1128/mSphereDirect.00190-17).

Male interferon receptor deficient mice (IFNAR −/−), aged between 6-8 weeks were vaccinated via the intramuscular route with either the single-vectored vaccine, ZIKV/CHIKV (SCV1002) or the empty control vaccine (SCV105) at week 0 at $10^6$ PFU per mouse.

Groups of mice were bled at 4 weeks post-vaccination to check for seroconversion to the vaccine. At 6 weeks post-vaccination, male mice were infected with Zika Natal strain at $10^4$ $CCID_{50}$ units via subcutaneous infection. Following infection, mice were bled daily between days 1 to 5 to check for viraemia At day 21 post-infection mice were culled, testes were harvested to assess ZIKV RNA using quantitative real-time PCR using primers targeting the prM gene. RNA was extracted using Trizol (Life Technologies) following the manufacturers' instructions. cDNA was synthesised using the Biorad iscript reverse transcriptase supermix following the manufacturers' instructions. Quantitative real-time was performed using the Biorad iTaq Universal Sybr green supermix kit. Real time PCR results were quantitated relative to levels of the house keeping gene RPL13.

Male mice vaccinated with SCV1002 (CHIK/ZIKA vaccine) were not able to replicate Zika virus following challenge with Zika virus Natal strain as shown by minimal detection of viraemia post-challenge. However, as expected the SCV105 (SCV vector only) vaccinated mice were able to replicate Zika virus as shown by the high level of viraemia seen in the first 3 days after challenge.

Vaccination with SCV1002 (CHIK/ZIKA) was also able to reduce the amount of viral RNA seen in testes at Day 21 compared to mice vaccinated with the control vaccine, SCV105.

BIBLIOGRAPHY

Altschul et al. (1997) *Nucleic Acids Research* 25:3389-3402
Ausubel et al. (1999) Current Protocols in Molecular Biology (Supplement 47), John Wiley & Sons, New York
Boshart et al. (1985) *Cell* 41:521
Brooks et al. (1995) *J. Virol.* 69(12):7688-7698
Dijkema et al. (1985) *EMBO J.* 4:761
Drillien R, et al. (1978) *J Virol.* 28(3):843-50
Gorman et al., (1982) *Proc. Natl. Acad. Sci. USA* 79:6777
Ham R G. (1965) *Proc. Natl. Acad. Sci.* USA 53: 288-293
Hsiao J C, et al. (2006) *J. Virol.* 80(15):7714-28
Kibler et al. (2011) *PLOSONE* 6(11)
Meisinger-Henschel et al. (2007) *J. Gen. Virol.* 88(12):3249-3259
Murphy et al. (1995) Virus Taxonomy Springer Verlag: 79-87
Puck T T, et al. (1958) *J. Exp. Med.* 108:945-956
Sambrook et al. (1989) Molecular Cloning: A Laboratory Manual, 2nd ed., Cold Spring Harbor Press, Plainsview, N.Y.
Shisler et al. (2004) *J. Virol.* 78(7):3553-3560
Spehner D, et al. (1988) *J Virol.,* 62(4):1297-1304
Werden S J, et al. (2008) Chapter 3: Poxvirus Host Range Genes. In: Advances in Virus Research, 71

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10905759B2). An electronic copy of the "Sequence Listing" will also be available from the USPTO upon request and payment of the fee set forth in 37 CFR 1.19(b)(3).

The invention claimed is:

1. An immunogenic composition comprising a pharmaceutically acceptable carrier and an attenuated poxvirus, wherein the attenuated poxvirus genome comprises a nucleic acid sequence encoding the 26S subgenomic polyprotein of chikungunya virus and a nucleic acid sequence encoding the PrME polyprotein of Zika virus and further comprises deletion of at least one gene which encodes an endogenous essential assembly or maturation protein and/or increases immunogenicity of the composition.

2. An immunogenic composition comprising a pharmaceutically acceptable carrier and an attenuated poxvirus, wherein the attenuated poxvirus genome comprises a nucleic acid sequence encoding the PrME polyprotein of Zika virus and further comprises deletion of at least one gene which encodes an endogenous essential assembly or maturation protein and/or increases immunogenicity of the composition.

3. The immunogenic composition of claim 1, wherein the attenuated poxvirus is selected from the group consisting of vaccinia, cowpox, Modified Vaccinia Ankara (MVA), NYVAC, avipox, canarypox and fowlpox.

4. The immunogenic composition of claim 1, wherein the gene which encodes an endogenous essential assembly or maturation protein and/or increases immunogenicity of the composition is a poxvirus D13L gene.

5. The immunogenic composition of claim 1, wherein gene which encodes an endogenous essential assembly or maturation protein and/or increases immunogenicity of the composition is a poxvirus K1L gene.

6. The immunogenic composition of claim 1, wherein gene which encodes an endogenous essential assembly or maturation protein and/or increases immunogenicity of the composition is a poxvirus A39R gene.

7. The immunogenic composition of claim 1, wherein the genes which encode an endogenous essential assembly or maturation protein and/or increases immunogenicity of the composition are poxvirus B7R-B8R genes.

8. The immunogenic composition of claim 1, wherein the attenuated poxvirus genome comprises a deletion in the poxvirus D13L gene, the A39R gene and the B37R-B8R genes.

9. The immunogenic composition of claim 1, wherein the pharmaceutically acceptable carrier comprises an adjuvant.

10. The immunogenic composition of claim 9, wherein the adjuvant is selected from the group consisting of aluminium hydroxide, aluminium phosphate, potassium aluminium sulfate, calcium phosphate hydroxide, Freund's complete adjuvant, Freund's incomplete adjuvant, iscoms, and iscomatrix.

11. A method of inducing a protective immune response in a subject against chikungunya and smallpox virus infection, smallpox and Zika virus infection and/or chikungunya, smallpox and Zika virus infection the method comprising administering to the subject the immunogenic composition of claim 1.

* * * * *